United States Patent [19]

Kondo et al.

[11] 4,073,687
[45] Feb. 14, 1978

[54] ENZYMATIC ACYLATION TO AFFORD β-LACTAM ANTIBIOTICS

[75] Inventors: Eiji Kondo, Ikeda; Takashi Mitsugi, Izumiotsu, both of Japan

[73] Assignee: Shionogi & Co., Ltd., Osaka, Japan

[21] Appl. No.: 686,219

[22] Filed: May 12, 1976

[30] Foreign Application Priority Data

May 14, 1975 Japan .................................. 50-57844

[51] Int. Cl.² ................................................ C12D 1/02
[52] U.S. Cl. ................................ 195/36 P; 195/36 C
[58] Field of Search ......................... 195/29, 36 P, 36 C

[56] References Cited

U.S. PATENT DOCUMENTS

| 3,761,354 | 9/1973 | Abe et al. ........................ 195/29 |
| 3,763,000 | 10/1973 | Abe et al. ........................ 195/29 |
| 3,816,253 | 6/1974 | Takahashi et al. ................ 195/29 |
| 3,862,004 | 1/1975 | Takahashi et al. ................ 195/29 |
| 3,962,036 | 6/1976 | Liersch et al. .................... 195/29 |

*Primary Examiner*—Lionel M. Shapiro
*Assistant Examiner*—Robert J. Warden
*Attorney, Agent, or Firm*—Wenderoth, Lind & Ponack

[57] ABSTRACT

Penicillin or cephalosporin antibiotics represented by following formula:

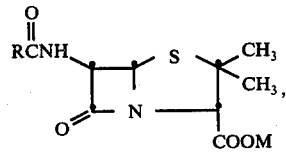

-continued

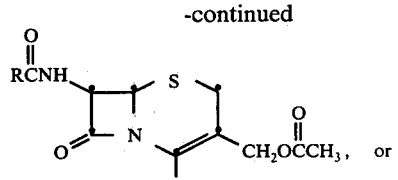

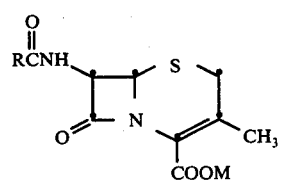

[where

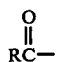

is an acyl group derived from an α-amino acid, N-ammonium salt of α-amino acid, or N—($C_1$ to $C_{10}$) acyl-α-amino acid; COOM is carboxy or carboxylate salt group]

are prepared by treating an amino compound selected from a group consisting of 6-aminopenicillanic acid, 7-aminocephalosporanic acid, 7-aminodeacetoxycephalosporanic acid, and their salts with an ester represented by following formula:

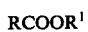

[where

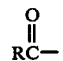

is as defined above and $R^1$ is a ($C_1$ to $C_{10}$) alkyl group]

by enzymatic acylation effected with mycelium or mycelium preparation from a microorganism belonging to genus *Aphanocladium* or *Cephalosporium*.

11 Claims, No Drawings

ENZYMATIC ACYLATION TO AFFORD β-LACTAM ANTIBIOTICS

This invention relates to a process for preparing penicillin or cephalosporin antibiotics represented by the following formula:

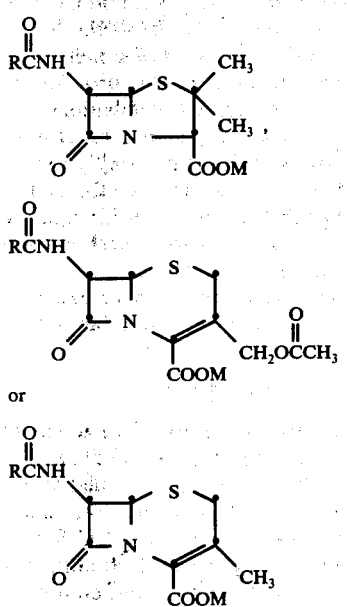

[where

is an acyl group derived from an α-amino acid, N-ammonium salt of α-amino acid, or N-($C_1$ to $C_{10}$) acyl-α-amino acid; COOM is a carboxy or carboxylate salt group]
by treating an amino compound selected from the group consisting of 6-aminopenicillanic acid, 7-aminocephalosporanic acid, 7-aminodeacetoxycephalosporanic acid and their salts, with an ester represented by the following formula:

RCOOR¹

[where

is as defined above and R¹ is a ($C_1$ to $C_{10}$) alkyl group] by enzymatic acylation effected with mycelium or mycelium preparation from a microorganism belonging to genus *Aphanocladium* or *Cephalosporium*.

Several penicillins and cephalosporins have been reported to be synthesized by enzymatic acylation to form α-aminoacyl side chains [South Africa Pat. No. 62/3870; U.S. Pat. No. 3,152,050; German patent application Nos. 1,945,607 and 2,050,982; Dutch patent application No. 7,117,613; French Pat. No. 2,188,608; Belgian Pat. No. 808,288; Japanese patent application (Publication) Nos. 47-25,388, 48-35,090, 49-13,393, and 49-62,695; and other publications].

It has now been found that this acylation can also take place by the action of fungal microorganisms belonging to genus *Aphanocladium* or *Cephalosporium*, and the action is, contrary to common bacterial actions, irreversible in nature.

Among said amino compounds are 6-aminopenicillanic acid, 7-aminocephalosporanic acid, 7-aminodeacetoxycephalosporanic acid, and their salts. Illustrative of the salts are those at the carboxyl group, including such salts as alkali metal salts, alkaline earth metal salts, and tertiary amine salts; and those at the amino group, including such mineral acid salts as hydrochloride, hydrogen sulfate, and hydrogen carbonate. Preferable salts are alkali metal salts at the carboxy group.

The said amino acid can be glycine, phenylglycine, cyclohexadienylglycine, cyclohexylglycine, thienylglycine, furylglycine, hydroxyphenylglycine, chlorophenylglycine, cyanophenylglycine, alanine, phenylalanine, methionine, serine, tryptophan, valine, leucine, threonine, asparagine, lysine, α-aminobutyric acid, and other natural or artificial amino acids. They can be either D- or L-isomer, or mixtures thereof including racemic mixtures. Preferable examples are D-α-phenylglycine, D-α-(1,4-cyclohexadienyl)glycine, D-α-(p-hydroxyphenyl)glycine, D-α-(2-thienyl)glycine, and D-α-(3-thienyl)glycine.

The said ester can be ($C_1$ to $C_{10}$) alkyl ester, among which methyl, ethyl, and propyl ester are more preferable. The ester can be N-ammonium salt of said amino acids, for example, mineral acid addition salt at the amino group.

Preferable esters are mineral acid addition salts of ($C_1$ to $C_5$) alkyl ester of said α-amino acid. Other forms of preferable ester are ($C_1$ to $C_5$) alkanoic acid salts at the α-amino group of the said amino acids.

The products of this invention are compounds represented by formula I, II, or III above. Representative carboxylates are alkali metal salts, alkaline earth metal salts, and tertiary amine salts; and representative N-ammonium salts are mineral acid salt, and ($C_1$ to $C_{10}$) alkanoic acid salts. The products can be in N—($C_1$ to $C_{10}$) acylated forms, in which the acyl group can be alkanoyl, aroyl, carbalkoxy, carbaralkoxy, or like acyl groups.

Preferable products include Ampicillin, Cefalexin, Epicillin, Cefradine, Amoxycillin, Cefaloglycin, or their salts.

The products prepared by this invention are useful as antibacterials for the treatment of diseases caused by bacterial infections sensitive to the drugs. Several of the products are currently in clinical use. The compounds are also useful for disinfection of animals, plants, or materials, as are known well by those skilled in the art. The methods for their use or application are also known in medical, veterinary, poultry, horticultural, botanical, or other related fields. They are also useful intermediates, e.g., for other antibiotics.

The process of this invention is carried out by contacting said amino compound with said ester in the presence of a microorganism belonging to the genus *Aphanocladium* or *Cephalosporium*, or its mycelium preparations.

The microorganism belonging to the genus *Aphanocladium* employed in this invention can be known *Aphanoclacium aranearum* (Petch) Grams. especially, *Aphanocladium aranearum* MFC-52, (the strain ATCC 20453).

The microorganisms belonging to the genus *Cephalosporium* employed in this invention can be known *Cephalosporium coremioides Raillo* especially *Cephalosporium coremioides Raillo,* the strain IFO-8579 available to the public.

All natural and artificial variants, mutants or adapted strains derived from the microorganisms belonging to genus *Aphanocladium* or *Cephalosporium* showing the desired enzymatic activity are included in the scope of the microorganisms suitable for use in this invention.

These microorganisms can be propagated as follows, to use in this invention: The microorganisms are inoculated in a culture medium and aerobically stirred by shaking culture, stationary culture, or culture under aeration to provide the said mycelium. The culture medium can be conventional ones, and can obtain such carbon and nitrogen sources as bouillon, yeast extract, peptone, corn steep liquor, sugar, organic acid, amino compounds, nitrate, and other carbon and nitrogen sources; such inorganic salts as phosphate, sulfate, and metal salts; and such essential elements necessary for the growth of the fungus as vitamine and amino acids. In particular, the incubation can be carried out in an aerobic condition at pH of between about 5 to 8, preferably about 6 to 7, and temperature of between about 20° to about 40° C, for about 3 hours to 10 days. Three respresentative media for the propagation consist of aqueous solution (pH about 7.0) containing (a) glucose (3.5%), peptone (2.0%), corn steep liquor (0.3%); (b) glucose (2.0%), peptone (1.0%), bouillon (0.3%), yeast extract (0.2%), sodium chloride (0.1%); or (c) cane sugar (3.0%), golden protein (1.5%), corn steep liquor (1.5%), DL-methionine (0.5%), and calcium carbonate (0.15%).

The mycelium preparation includes all of the preparations available for using penicillin- or cephalosporin-amidase activity of the said microorganisms, for example, washed mycelium obtained by isolating the mycelium propagated as above from the nutrient solution by filtration or centrifugation, followed by washing with water or aqueous solution; mycelium homogenate obtained by crushing the cells of the mycelium; crude or purified enzyme possibly bound on an insoluble material; or extracellular enzyme in the nutrient solution of the propagated medium or its preparation. The propagated medium can also be used for carrying out the reaction of this invention.

The substrates can be employed in a form of powder, suspension, solution of hydrophilic organic solvent or aqueous solution. Preferable hydrophilic organic solvents are alcohol, acetone, and glycol. These solvents are employed at a concentration which does not inhibit the desired enzymatic reaction.

The reaction is carried out in an aqueous solution. Distilled water, buffer solutions, or propagated nutrient media themselves can be used as preferable aqueous solution or aqueous medium for the reaction. Aerobic condition is not essential. When the microorganisms contain 62 -lactamase, peniciilins can be added to inhibit the unfavorable activity. Preferable conditions for the reaction are pH of between about 5 and about 8, a temperature of from about 20° C to about 40° C, and shaking or agitation period for from about 5 to about 50 hours. These conditions vary depending on the sort of starting materials, concentration, sort of microorganism used, character of the culture medium, and working up methods. If desired, acid, base, or buffer solution can be added to the reaction mixture when the pH of the medium changes unfavorably during the reaction. The concentration of the starting material is from about 0.1 to about 5%, preferably less than 2%.

After the reaction, the mycelium, mycelium preparation or insoluble materials are separated from the reaction mixture by, e.g., filtration, centrifugation, adsorption, denaturation, or the combination thereof; and the products so formed can be separated by various methods such as adsorption, fractional extraction, concentration, deposition, precipitation, or like methods, and can be isolated and purified by conventional methods in the art, e.g., recrystallization, adsorption, chromatography, ion-exchange, reprecipitation, lyophillization, countercurrent distribution, and like methods. During the working up, the hydrogen in the carboxy group can be replaced by another cation to form a salt, or the side chain amino group can form a salt with, e.g., mineral acid, sulfonic acid containing 1 to 10 carbon atoms, or other acids.

The following examples are given to explain more detailed embodiments of this invention, but not to limit the scope thereof.

EXAMPLE 1

In a medium (100 ml) consisting of an aqueous solution (pH 7.0) containing glucose (3.5%), peptone (2.0%), corn steep liquor (0.3%), is inoculated *Aphanocladium aranearum* ATCC 20453, and the inoculated medium is cultured with shaking at 28° C for 3 days. The broth is filtered through a cloth to collect mycelium, washed with deionized water, and compressed to remove excess water.

About 9 g of the wet mycelium so obtained is suspended in deionized water (100 ml) containing 7-aminodeacetoxycephalosporanic acid (0.1 g) and D-α-phenylglycine methyl ester hydrochloride (0.5 g). The suspension is adjusted to pH 6.0 with an aqueous solution of 1N-sodium carbonate, and stirred at 30° C for 16 hours, while the pH is maintained at 6.0. The suspension is then filtered to remove mycelium, and stored at 0° C overnight. After filtering off the crystallized D-α-phenylglycine, the filtrate is adjusted to pH 4.0 with 1N-hydrochloric acid. This preparation is passed through an ion-exchange resin (Dowex 50W $\times$ 8) column (60 ml) treated with 0.2M citric acid buffer solution (pH 4.5), and the column is washed with the 0.2M citric acid buffer. A small amount of D-α-phenylglycine methyl ester and 7-aminodeacetoxycephalosporanic acid is recovered from the first fraction. To the next antibiotically active fraction is added 3% by weight of active carbon, and the mixture is filtered after stirring for 30 minutes. The active carbon is collected and eluted with 50% methanol, and the eluate is concentrated under reduced pressure. The residue is treated with methanol and ethyl acetate to give the solid (53 mg) of the crude product.

The white powder is recrystallized from a mixture of
    methanol and ethyl acetate, affording 23.8 mg of
    7β-(D-α-phenylglycyl)aminodeacetoxycephalos-
    poranic acid (Cefalexin) monohydrate.
    m.p. 185°–190° C (decomp.)
    I.R. $\nu_{max}^{Nujol}$ 1763, 1690, 1590 cm$^{-1}$.

EXAMPLE 2

Under the same condition as described in Example 1, 6-aminopenicillanic acid (0.1 g) is reacted with D-α-phenylglycine methyl ester hydrochloride (0.5 g) using *Aphanocladium aranearum* ATCC 20453. The product is adsorbed on active carbon after adjusting the pH of the reaction mixture to 6.0 with an aqueous solution of sodium hydroxide. Following the procedure set forth in Example 1, the product is eluted from the active carbon, and recrystallized to give 37.9 mg of sodium 6β-(D-α-phenylglycyl)aminopenicillanate (Sodium ampicillin).

m.p. 221°–226° C (decomp.)

I.R. $\nu_{max}^{Nujol}$ 1770, 1691, 1600 cm$^{-1}$.

EXAMPLE 3

Under the condition similar to that described in Example 1, 7-aminodeacetoxycephalosporanic acid (0.1 g) is reacted with D-α-phenylglycine methyl ester hydrochloride using *Aphanocladium aranearum* ATCC 20453 (30° C, 16 hours, pH 6.0). The paper disk microbiological assay of the reaction mixture using *Bacillus subtilis* PCI-219, shows that 0.118 g of Cefalexin is produced. Yield: 72.8%.

EXAMPLE 4

Under the condition similar to that described in Example 1, 7-aminodeacetoxycephalosporanic acid (0.25 g) is reacted with D-α-phenylglycine hydrochloride methyl ester using *Aphanocladium aranearum* ATCC 20453 (30° C, 23 hours, pH 6.0). Cefalexin (0.292 g) is found in the reaction mixture by microbiological assay. Yield: 71.9%.

EXAMPLE 5

Under the condition similar to that of Example 1, 7-aminodeacetoxycephalosporanic acid (0.3 g) is reacted with D-α-phenylglycine methyl ester hydrochloride using *Aphanocladium aranearum* ATCC 20453 (30° C, 19 hours, pH 6.0). Cefalexin (0.338 g) is found in the reaction mixture by microbiological assay. Yield: 69.6%.

EXAMPLE 6

Following the procedure set forth in Example 1, 6-aminopenicillanic acid is reacted with D-α-phenylglycine methyl ester hydrochloride under the condition given in the following table, using *Aphanocladium aranearum* ATCC 20453. The amount of sodium salt of Ampicillin produced in the reaction mixture is measured by microbiological assay to give the values shown in the same table.

| Amount of Substrate (g/dl) | | Reaction Time (hr) | Yield of Ampicillin | |
|---|---|---|---|---|
| 6-APA[1] | PGM[2] | | (g/dl) | (%) |
| 0.1 | 1.0 | 17 | 0.1304 | 75.9 |
| 0.2 | 2.0 | 16 | 0.2380 | 69.3 |
| 0.3 | 3.0 | 15 | 0.4460 | 86.6 |

(30° C, pH 6.0)
[1] 6-aminopenicillanic acid
[2] D-α-phenylglycine methyl ester hydrochloride

EXAMPLE 7

Under the condition similar to that of Example 1, 7-aminodeacetoxycephalosporanic acid (0.1 g) is reacted with D-α-(1,4-cyclohexadienyl)glycine methyl ester hydrochloride using *Aphanocladium aranearum* ATCC 20453 (30° C, 22 hours, pH 6.0). In the reaction mixture is found 7β-D-α-(1,4-cyclohexadienyl)glycylaminodeacetoxycephalosporanic acid (Cephradin, Rf: 0.35, 0.109 g) when detected by microbiological assay. Yield: 67.3% (Calculated as Cefalexin).

EXAMPLE 8

Under the condition similar to that of Example 7, 6-aminopenicillanic acid (0.1 g) is reacted with D-α-(1,4-cyclohexadienyl)glycine methyl ester hydrochloride using *Aphanocladium aranearum* ATCa 20453 (30° C, 22 hours, pH 6.0). In the reaction mixture is found 6β-D-α-(1,4-cyclohexadienyl)glycylaminopenicillanic acid (Epicillin) (0.064 g) when detected by microbiological assay. Yield: 37.4% (calculated as Ampicillin).

EXAMPLE 9

Under the condition similar to that of Example 1, 7-aminodeacetoxycephalosporanic acid (0.1 g) is reacted with amino acid derivatives shown in the following table, using *Aphanocladium aranearum* ATCC 20453 at 28° C for 18 hours to give the corresponding 7β-(αaminoacyl)aminodeacetoxycephalosporanic acid derivatives. The Rf values of each product on thin-layer chromatogram over silica gel are also shown in the table (developed with a mixture of ethyl acetate, acetic acid, and water (3:1:1 v/v)).

| Starting amino acid derivatives | Rf of products |
|---|---|
| DL-methionine methyl ester | 0.57 |
| DL-alanine methyl ester | — |
| DL-phenylalanine methyl ester | — |
| DL-serine methyl ester | — |
| DL-tryptophan methyl ester | 0.39 |
| DL-valine methyl ester | — |
| DL-α-aminobutyric acid methyl ester | — |
| α-N-benzoyl-DL-alanine methyl ester | 0.84 |
| α-N-carbobenzoxy-D-phenylglycine methyl ester | 0.53 |

EXAMPLE 10

Under the conditions similar to that of Example 9, 6-aminopenicillanic acid (0.1 g) is reacted with the amino acid derivatives shown in the following table, using *Aphanocladium aranearum* ATCC 20453 at 28° C for 18 hours to give the corresponding 6β-(α-aminoacyl)aminopenicillanic acid derivatives. The Rf values of each product on thin-layer chromatogram over silica gel developed with a mixture of n-butanol, ethanol, and water (4:1:1 v/v) and the yield determined by microbiological assay are shown in the following table.

| Starting amino acid derivatives | Production (γ/ml) calculated as Ampicillin | Rf of Products |
|---|---|---|
| DL-methionine methyl ester | 13 | 0.27 |
| DL-alanine methyl ester | 31 | — |
| DL-phenylalanine methyl ester | + | — |
| DL-serine methyl ester | 25 | 0.32 |
| DL-tryptophan methyl ester | 16 | — |
| DL-valine methyl ester | 36 | — |
| DL-α-aminobutyric acid methyl | 63 | 0.13 |
| α-N-benzoyl-DL-alanine methyl ester | 108 | 0.35 |
| α-N-carbobenzoxy-D-phenyglycine methyl ester | 22 | 0.48 |

EXAMPLE 11

Under the condition similar to that of Example 1, 6-aminopenicillanic acid (0.1 g) is reacted with D-α-(p- hydroxyphenyl)glycine methyl ester hydrochloride (1 g) using *Aphanocladium aranearum* ATCC 20453 at 30° C for 23 hours at pH 6.0. Thin-layer chromatogram of the reaction mixture shows a spot corresponding to 6β-D-α-(p-hydroxyphenyl)glycinamidopenicillanic acid (Amoxycillin).

EXAMPLE 12

The mycelium of *Aphanocladium aranearum* ATCC 20453 is homogenated by using 1.5 weights of alumina, diluted with M/15-phosphate buffer (pH 5.0, 6.0, and 7.0) and centrifuged. Ammonium sulfate is added to the supernatant to provide a concentration of 60%, and enzyme fraction is salted out. The obtained precipitate is dissolved in the buffer solution mentioned above, and dialyzed overnight to give crude enzyme solution. This process is carried out at a temperature of 0° to 4° C.

The enzyme solution (1 ml) is reacted on 7-aminodeacetoxycephalosporanic acid and D-α-phenylglycine methyl ester hydrochloride at 37° C. The amount of the obtained Cefalexin in the reaction mixture determined by microbiological assay

| Amount of Substrate (mg/ml) | | Concentration of enzyme protein (mg/ml) | pH of medium | Produced Cefalexin (γ/ml) | |
|---|---|---|---|---|---|
| 7-ADCA[1] | PGM[2] | | | 1 hr. | 3 hrs. |
| 1.0 | 2.5 | 5.0 | 5.0 | 82 | 69 |
| 1.0 | 2.5 | 5.0 | 6.0 | 316 | 500 |
| 1.0 | 2.5 | 5.0 | 7.0 | 177 | 145 |
| 1.0 | 5.0 | 5.0 | 7.0 | 180 | 170 |
| 3.0 | 7.5 | 2.0 | 6.0 | 393 | 643 |
| 1.0 | 2.5 | 2.0 | 6.0 | 205 | 282 |
| 1.0 | 5.0 | 2.0 | 6.0 | 247 | 429 |

[1]7-aminodeacetoxycephalosporanic acid
[2]D-α-phenylglycine methyl ester hydrochloride

EXAMPLE 13

The crude enzyme solution obtained by the method of Example 12 (1 ml) is reacted on 6-aminopenicillanic acid and D-α-phenylglycine methyl ester hydrochloride at 37° C. The amount of ampicillin produced in the reaction mixture is measured by microbiological assay, and the results are shown in the following table.

| Amount of Substrate (mg/ml) | | Concentration of enzyme protein (mg/ml) | pH of medium | Produced Ampicillin (γ/ml) | |
|---|---|---|---|---|---|
| 6-APA[1] | PGM[2] | | | 1 hr. | 3 hrs. |
| 1.0 | 2.5 | 5.0 | 5.0 | 126 | 126 |
| 1.0 | 2.5 | 5.0 | 6.0 | 465 | 540 |
| 1.0 | 2.5 | 5.0 | 7.0 | 224 | 255 |
| 1.0 | 5.0 | 5.0 | 7.0 | 210 | 221 |
| 0.5 | 2.5 | 2.0 | 6.0 | 191 | 264 |
| 3.0 | 7.5 | 2.0 | 6.0 | 890 | 1370 |
| 1.0 | 2.5 | 2.0 | 6.0 | 300 | 475 |
| 1.0 | 5.0 | 2.0 | 6.0 | 379 | 695 |

[1]6-aminopenicillanic acid
[2]D-α-phenylglycine methyl ester hydrochloride

EXAMPLE 14

Under the condition similar to that of Example 1, 7-aminocephalosporanic acid (0.25%) is reacted with D-α-phenylglycine methyl ester hyrochloride (2.5 g) using *Aphanocladium aranearum* ATCC 20453 (30° C, 23 hours, pH 6.0). Spots of cephaloglycine and deacetylcephaloglycine are shown on thin-layer chromatogram, and the amount of Cefaloglycin formed is 0.072 g when determined by microbiological assay.

EXAMPLE 15

To a sterilized medium (100 ml) consisting of aqueous solution (pH 7.0) containing glucose (3.5%), peptone (2.0%), and corn steep liquor (0.3%), is inoculated *Cephalosporium coremioides* IFO-8579, and the medium is shaken at 28° C for 3 days. The broth is centrifuged to collect the mycelia, which is washed with deionized water.

The wet mycelium so obtained is suspended in M/30-phosphate buffer (pH 6.0), containing 7-aminodeacetoxycephalosporanic acid and D-α-phenylglycine methyl ester hydrochloride (0.4 g), at 28° C for 24 hours. The amount of Cefalexin formed in the reaction mixture is 0.095 g when determined by microbiological assay.

EXAMPLE 16

Under the condition similar to that of Example 15, 6-aminopenicillanic acid is reacted with D-α-phenylglycine methyl ester hydrochloride using the mycelium obtained in the procedure of Example 15 to produce 0.08 g of Ampicillin when determined by microbiological assay.

What we claim is:

1. A process for preparing a penicillin or cephalosporin antibiotic of the formula

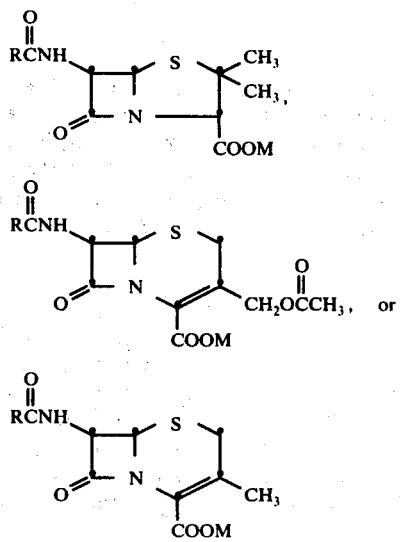

wherein

RC— is an acyl group derived from an α-amino acid, an N-ammonium salt of an α-amino acid or an N—($C_1$ to $C_{10}$) acyl-α-amino acid and COOM is carboxy or a carboxylate salt group, which comprises reacting an amino compound selected from the group consisting of 6-aminopenicillanic acid, 7-aminocephalosporanic acid, 7-aminodeacetoxycephalosporanic acid and salts thereof with an ester of the formula

RCOR' wherein

is as defined above and $R^1$ is a ($C_1$ to $C_{10}$) alkyl group, by enzymatic acylation effected with mycelium or mycelium preparation from a microorganism belonging to the genus *Aphanocladium* or to *Cephalosporium coremioides* Raillo.

2. A process according to claim 1, wherein the amino compound is selected from the group consisting of 6-aminopenicillanic acid, b 7-aminocephalosporanic acid, 7-aminodeacetoxycephalosporanic acid and their alkali metal salts.

3. A process according to claim 1, wherein the α-amino acid is selected from the group consiting of glycine, phenylglycine, cyclohexadienylglycine, cyclohexylglycine, thienylglycine, furylglycine, hydroxyphenylglycine, chlorophenylglycine, cyanophenylglycine, alanine, phenylalanine, methionine, serine tryptophan, valine, leucine, threonine, asparagine, lysine, α-aminobutyric acid, and their N-benzoyl-or N-carbobenzoxy derivatives.

4. A process according to claim 1, wherein the α-amino acid is selected from D-α-phenylglycine, D-α-(1,4-cyclohexadienyl)glycine, D-α-(p-hydroxyphenyl)glycine, D-α-(2-thienyl)glycine, and D-α-(3-thienyl)glycine.

5. A process according to claim 1, wherein the ester is a ($C_1$ to $C_5$) alkyl ester of a mineral acid addition salt of said α-amino acid.

6. A process according to claim 1, wherein the microorganism is *Aphanocladium aranearum* (Petch) Grams., ATCC 20453.

7. A process according to claim 1, wherein the microorganism is *Cephalosporium coremioides* Raillo., IFO-8579.

8. A process according to claim 1, wherein the mycelium preparation is a washed mycelium.

9. A process according to claim 1, wherein the mycelium preparation is a crude or purified enzyme.

10. A process according to claim 1, wherein the reaction is carried out at a pH from of 5.0 to 8.0.

11. A process according to claim 1, wherein said penicillin or cephalosporin antibiotic is Ampicillin, Epicillin, Amoxycillin, Cefalexin, Cefradine, Cefaloglycin or a salt thereof.

* * * * *